(12) United States Patent
Bianchi et al.

(10) Patent No.: US 8,853,425 B2
(45) Date of Patent: Oct. 7, 2014

(54) PROCESS FOR THE PREPARATION OF BENZODITHIOPHENE COMPOUNDS

(71) Applicant: ENI S.p.A., Rome (IT)

(72) Inventors: Gabrielle Bianchi, L'Aquila (IT); Giuliana Schimperna, Novara (IT)

(73) Assignee: Eni S.p.A., Roma (IT)

( * ) Notice: Subject to any disclaimer, the term of this patent is extended or adjusted under 35 U.S.C. 154(b) by 0 days.

(21) Appl. No.: 14/182,787

(22) Filed: Feb. 18, 2014

(65) Prior Publication Data

US 2014/0235874 A1    Aug. 21, 2014

(30) Foreign Application Priority Data

Feb. 21, 2013   (IT) .............................. MI2013A0248

(51) Int. Cl.
   *C07D 495/04* (2006.01)
   *H01L 51/00* (2006.01)

(52) U.S. Cl.
   CPC .................................. *H01L 51/0074* (2013.01)
   USPC .......................................................... 549/43

(58) Field of Classification Search
   USPC .......................................................... 549/43
   See application file for complete search history.

(56) References Cited

PUBLICATIONS

Italian Search Report issued May 23, 2013 in Italian Application MI2013 0248, filed on Feb. 21, 2013 ( with English Translation of Categories of Cited Documents).

Hiroyuki Watanabe et al. " Synthesis of Alkylated Benzo [2,1-b : 3,4-b'] dithiophenes by Annulative Coupling and Their Direct Arylation under Palladium Catalysis", Chemistry Letters vol. 36, No. 11, 2007 2 pages.

Richard C. Larock et al. "Synthesis of Polycyclic Aromatic Hydrocarbons by the Pd-Catalyzed Annulation of Alkynes", J. Org Chem, 62, 1997, 2 pages.

Masaki Shimizu et al. "Palladium-Catalyzed double cross-coupling reaction of 1,2-bis (pinacolatoboryl) alkenes and—arenes with 2,2'-dibromobiaryls: annulative approach to functionalized polycyclic aromatic hrydocarbons", Tetrahedron 67, 2011, 13 pages.

*Primary Examiner* — Kristin Vajda

(74) *Attorney, Agent, or Firm* — Oblon, Spivak, McClelland, Maier & Neustadt, L.L.P.

(57) ABSTRACT

The present invention relates to a process for the preparation of benzodithiophene compounds which comprises reacting a derivative of 3,3'-bithiophene with at least one internal alkyne. Said benzodithiophene compounds can be suitably functionalized and polymerized to give electron-donor compounds which can be used in photovoltaic devices such as, for example, photovoltaic cells, photovoltaic modules, solar cells, solar modules, on both rigid and flexible supports. Furthermore said benzodithiophene compounds can be advantageously used as spectrum converter in luminescent solar concentrators (LSCs). Said benzodithiophene compound can also be advantageously used as precursor of monomeric units in the preparation of semiconductor polymers.

23 Claims, No Drawings

PROCESS FOR THE PREPARATION OF BENZODITHIOPHENE COMPOUNDS

The present invention relates to a process for the preparation of benzodithiophene compounds. More specifically, the present invention relates to a process for the preparation of benzodithiophene compounds which comprises reacting a derivative of 3,3'-bithiophene with at least one internal alkyne.

Said benzodithiophene compounds can be suitably functionalized and polymerized to give electron-donor compounds which can be used in photovoltaic devices such as, for example, photovoltaic cells, photovoltaic modules, solar cells, solar modules, on both rigid and flexible supports. Furthermore said benzodithiophene compounds can be advantageously used as spectrum converters in Luminescent Solar Concentrators (LSCs). Said benzodithiophene compound can also be advantageously used as precursor of monomeric units in the preparation of semiconductor polymers.

Photovoltaic devices are devices capable of converting the energy of a light radiation into electric energy. At present, most photovoltaic devices which can be used for practical applications exploit the physico-chemical properties of photoactive materials of the inorganic type, in particular high-purity crystalline silicon. As a result of the high production costs of silicon, scientific research, however, has been orienting its efforts towards the development of alternative organic materials having a conjugated, oligomeric or polymeric structure, in order to obtain organic photovoltaic devices such as, for example, organic photovoltaic cells. Unlike high-purity crystalline silicon, in fact, said materials of an organic nature are characterized by a relative synthesis facility, a low production cost, a reduced weight of the relative organic photovoltaic devices, and also allow the recycling of said materials of the organic type at the end of the life cycle of the organic photovoltaic device in which they are used.

The advantages indicated above make the use of said materials of the organic type energetically and economically interesting in spite of possible lower efficiencies ($\eta$) of the organic photovoltaic devices thus obtained with respect to inorganic photovoltaic devices.

The functioning of organic photovoltaic devices such as, for example, organic photovoltaic cells, is based on the combined use of an electron-acceptor compound and an electron-donor compound. In the state of the art, the most widely used electron-acceptor compounds in organic photovoltaic devices are fullerene derivatives, in particular PC61BM(6,6-phenyl-$C_{61}$-butyric acid methyl ester) or PC71BM (6,6-phenyl-$C_{71}$-butyric acid methyl ester), which have reached the greatest efficiencies when mixed with electron-donor compounds selected from $\pi$-conjugated polymers such as, for example, polythiophenes ($\eta$>5%), polycarbazoles ($\eta$>6%), derivatives of poly-(thienothiophene)-benzodithiophene (PTB) ($\eta$>8%).

The basic conversion process of light into electric current in an organic photovoltaic cell takes place through the following steps:
1. absorption of a photon on the part of the electron-donor compound with the formation of an exciton, i.e. a pair of "electronic electron-gap (or hole)" charge transporters;
2. diffusion of the exciton in a region of the electron-donor compound as far as the interface with the electron-acceptor compound;
3. dissociation of the exciton in the two charge transporters: (electron (−) in the acceptor phase (i.e. in the electron-acceptor compound) and electronic gap (or hole) (+)) in the donor phase (i.e. in the electron-donor compound);
4. transporting of the charges thus formed to the cathode (electron, through the electron-acceptor compound) and anode (electronic gap (or hole), through the electron-donor compound), with the generation of an electric current in the circuit of the organic photovoltaic cell.

The photo-absorption process with the formation of the exciton and subsequent yielding of the electron to the electron-acceptor compound leads to the excitation of an electron from the HOMO (Highest Occupied Molecular Orbital) to the LUMO (Lowest Unoccupied Molecular Orbital) of the electron-donor compound, and subsequently the passage from this to the LUMO of the electron-acceptor compound.

As the efficiency of an organic photovoltaic cell depends on the number of free electrons that are generated by dissociation of the excitons which, in turn, can be directly correlated with the number of photons absorbed, one of the structural characteristics of electron-donor compounds which mostly influences said efficiency is the difference in energy existing between the HOMO and LUMO orbitals of the electron-donor compound, or the so-called band-gap. The maximum wave-length value at which the electron-donor compound is capable of collecting and effectively converting photons into electric energy, i.e. the so-called "light-harvesting" or "photon harvesting" process, depends on this difference. In order to obtain acceptable electric currents, the band-gap, i.e. the difference in energy between HOMO and LUMO of the donor compound, must not be too high to allow the absorption of the highest number of photons, but at the same time not too low as it could decrease the voltage at the electrodes of the device.

In the simplest way of operating, organic photovoltaic cells are produced by introducing a thin layer (about 100 nanometers) of a mixture of the electron-acceptor compound and electron-donor compound (architecture known as "bulk heterojunction"), between two electrodes, normally consisting of indium-tin oxide (ITO) (anode) and aluminium (Al) (cathode). In order to produce a layer of this type, a solution of the two components is generally prepared and a photoactive film is subsequently created on the anode [indium-tin oxide (ITO] starting from said solution, resorting to suitable deposition techniques such as, for example, "spin-coating", "spray-coating" "ink-jet printing" and the like. Finally, the counter-electrode [i.e. the aluminium cathode (Al)] is deposited on the dried film. Optionally, other additional layers capable of exerting specific functions of an electric, optical or mechanical nature, can be introduced between the electrodes and photoactive film.

Generally, in order to facilitate the electron gaps (or holes) in reaching the anode [indium-tin oxide (ITO)] and at the same time in blocking the transporting of electrons, thus improving the collection of the charges on the part of the electrode and inhibiting recombination phenomena, before creating the photoactive film, starting from the mixture of acceptor compound and donor compound as described above, a film is deposited, starting from an aqueous suspension of PEDOT:PSS [poly(3,4-ethylenedioxythiophene)polystyrene sulfonate], resorting to suitable deposition techniques such as, for example, "spin-coating", "spray-coating" "ink-jet printing" and the like. Finally, the counter-electrode [cathode (Al)] is deposited on the dried film.

The electron-donor compound which is most commonly used in the construction of organic photovoltaic cells is regio-regular poly(3-hexylthiophene) (P3HT). This polymer has optimal electronic and optical characteristics (good HOMO and LUMO orbital values, good molar adsorption coefficient), a good solubility in the solvents used in the construction of photovoltaic cells and a reasonable mobility of the electronic gaps.

Other examples of polymers which can be advantageously used as electron-donor compounds are: the polymer PCDTBT {poly[N-9"-heptadecanyl-2,7-carbazole-alt-5,5-(4',7'-di-2-thienyl-2',1',3'-benzothiadiazole]}, the polymer PCPDTBT {poly[2,6-(4,4-bis-(2-ethylhexyl)-4H-cyclopenta[2,1-b; 3,4-b']-dithiophene)-alt-4,7-(2,1,3-benzothiadiazole)]}.

Electron-donor compounds containing benzodithiophene units having a structure similar to poly(3-hexylthiophene) (P3HT) are also known, wherein the thiophene units, however, are planarized by means of benzene rings. This characteristic not only reduces the oxidation potential of said electron-donor compounds but also improves their stability to air and guarantees their rapid packing and consequently a high molecular order, during the formation of the photoactive film: this leads to excellent charge transporting properties [electrons or electronic gaps (holes)]. The use of electron-donor compounds containing benzodithiophene units therefore enables the production of photovoltaic devices having improved performances.

Electron-donor compounds containing benzodithiophene units are described, for example, by Huo L. et al. in the article: "Synthesis of a polythieno[3,4-b]thiophene derivative with a low-lying HOMO level and its application in polymer solar cells", *Chemical Communication*" (2011), Vol. 47, pages 8850-8852. This article describes the preparation of a polythieno[3,4-b]thiophene derivative by copolymerization between a planar benzodithiophene having a low HOMO value with a thieno[3,4-b]thiophene unit.

It is known that benzodithiophene and/or its isomers [e.g., benzo[1,2-b:4,5-b']dithiophene or (BDT) and benzo[2,1-b:3,4-b'] dithiophene or (BDP)], are compounds of great interest whose synthesis has been the object of many research.

Benzodithiophene and/or its isomers can generally be prepared by means of three different processes.

A first process comprises an annulation reaction known as McMurry reaction, of 3,3'-dialkanoyl-2,2'-dithiophene. This annulation reaction is generally carried out in the presence of catalysts containing titanium and zinc, at a temperature ranging from 60° C. to 80° C., in the presence of solvents such as, for example, tetrahydrofuran (THF), dioxane, for a time ranging from 8 to 12 hours. The yields to benzodithiophene and/or its isomers generally range from 30% to 90%.

Further details relating to said first process can be found, for example, in the article of Yoshida S. et al: "Novel Electron Acceptors Bearing a Heteroquinonoid System. 4. Syntheses, Properties, and Charge-Transfer Complexes of 2,7-Bis(dicyanomethylene)-2,7-dihydrobenzo[2,1-b:3,4-b'] dithiophene, 2,7-Bis(dicyanomethylene)-2,7-dihydrobenzo-[1,2-b:4,3-b']-dithiophene, and 2,6-Bis(dicyanomethylene)-2,6-dihydrobenzo-[1,2-b:4,5-b']-dithiophene", *Journal of Organic Chemistry*" (1994), Vol. 59, No. 11, pages 3077-3081. This article describes the preparation of a dicyanoalkylene-benzodithiophene starting from benzodithiophene isomers such as, for example, benzo[2,1-b:3,4-b']-dithiophene, benzo[1,2-b:4,3-b']-dithiophene, benzo[1,2-b:4,5-b']-dithiophene. Said benzodithiophene isomers can be obtained by the reaction of 2,2'-dithiophene-3,3'-dicarboxaldehyde with titanium tetrachloride ($TiCl_4$) and metal zinc (Zn), in anhydrous tetrahydrofuran.

Further details relating to this first process can also be found in the article of Rajca S. et al.: "Functionalized Thiophene-Based [7]Helicene: Chirooptical Properties versus Electron Delocalization", *Journal of Organic Chemistry*" (2009), Vol. 74, No. 19, pages 7504-7513. This article describes the preparation of an enantiomerically pure functionalized [7]helicene, deriving from a di(benzodithiophene) functionalized with four heptyl groups. The preparation of a benzodithiophene is also described, by the reaction of a 3,4-dibromothiophene with lithium diisopropylamide (LDA) to give a dilithiate derivative which is subsequently reacted with N-methoxy-N-methyl octanamide to give the corresponding diketone. Said diketone is subsequently reacted with titanium tetrachloride ($TiCl_4$) and metal zinc (Zn) obtaining benzodithiophene.

The second process comprises an annulation reaction between a diiodo-dithiophene and an excess of internal alkyne. Said reaction is generally carried out in the presence of catalysts containing palladium, at a temperature ranging from 120° C. to 140° C., in the presence of solvents such as, for example, N,N-dimethylformamide (DMF), toluene, o-xylene, for a time ranging from 4 hours to 48 hours. The yields generally range from 50% to 90%.

Further details relating to this second process can be found, for example, in the article of Watanabe H et al.: "Synthesis of Alkylated Benzo[2,1-b:3,4-b']dithiophenes by Annulative Coupling and Their Direct Arylation under Palladium Catalysis", *Chemistry Letters*" (2007), Vol. 36, No. 11, pages 1336-1337. This article describes the preparation of a dialkyl derivative of benzo[2,1-b:3,4-b']dithiophene by the reaction of 3,3'-diiodo-2,2'-dithiophene with 4-octyne, in the presence of N,N-dimethylformamide (DMF) and palladium(II)acetate $Pd(OAc)_2$ and N-methyl-N,N-dicyclohexylamine as catalyst.

The third process comprises an annulation reaction between a dibromo-dithiophene and a vic-bis-(pinacolatoboryl) alkene or a vic-bis(pinacolatoboryl)-phenanthrene. This reaction is generally carried out in the presence of catalysts containing palladium, at a temperature ranging from 60° C. to 80° C., in the presence of solvents such as, for example, tetrahydrofuran (THF), toluene, for a time ranging from 24 hours to 48 hours. The yields generally range from 50% to 90%.

Further details relating to this third process can be found, for example, in the article of Shimizu M. et al.: "Palladium-Catalyzed Annulation of vic-Bis(pinacolatoboryl)alkenes and -phenanthrenes with 2,2'-dibromobiaryls: Facile Synthesis of Functionalized Phenanthrenes and Dibenzo[g,p]-chrysenes", *Angewandte Chemie International Edition*" (2008), Vol. 47, pages 8096-8099. This article describes the preparation of a dialkyl-benzodithiophene by the reaction of a dibromo-dithiophene with a vic-bis(pinacolatoboryl)alkene in tetrahydrofuran (THF), in the presence of potassium carbonate ($K_2CO_3$) and tetrakis(triphenylphosphine)-palladium (0) [$Pd(PPh_3)_4$] as catalyst.

Although the above processes allow benzodithiophene and/or its isomers to be obtained with good yields, generally higher than or equal to 50%, they can, however, have various disadvantages. In particular:
  there are numerous synthesis steps for obtaining the desired final compound;
  toxic and explosive reagents are often used, such as, for example, titanium tetrachloride, lithium diisopropylamide (LDA), with consequent problems relating to the safety of both the environment and operators, with consequently higher costs for both production and disposal of the waste products.
  dihalogenated starting compounds are often used, such as, for example, diiodo-dithiophene or dibromo-dithiophene, which are generally costly and not particularly stable.

Processes for the preparation of polycyclic aromatic compounds through annulation reactions of aryl halides with internal alkynes, in the presence of palladium compounds as catalysts, are also known in the art.

Larock R. C. et al., for example, in the article: "Synthesis of Polycyclic Aromatic Hydrocarbons by the Pd-Catalyzed Annulation of Alkynes", "*Journal of Organic Chemistry*" (1997), Vol. 62, No. 22, pages 7536-7537, describe an annulation reaction with internal alkynes according to the following Scheme 1:

Scheme 1

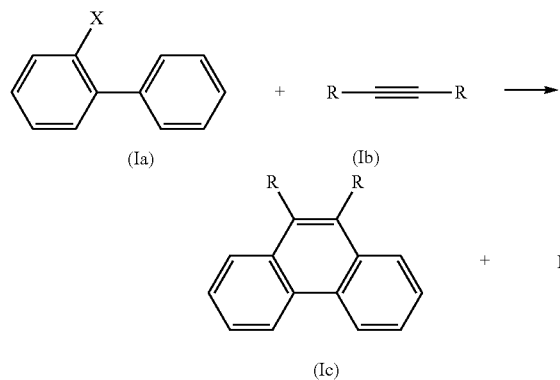

wherein an aryl halide having formula (Ia) such as, for example, 2-iodobiphenyl, is reacted with an internal alkyne having formula (Ib) such as, for example, diphenylacetylene, in the presence of a catalyst containing palladium such as, for example, palladium(II)acetate ([Pd(OAc)$_2$]), a solvent such as, for example, dimethylformamide (DMF), and a base such as, for example, sodium acetate (NaOAc), obtaining a disubstituted phenanthrene having formula (Ic).

Huang H. et al., in the article "Palladium-catalyzed three-component domino reaction for the preparation of benzo[b]thiophene and related compounds", "*Organic and Biomolecular Chemistry*" (2011), Vol. 9, pages 5036-5038, describe a three-component domino annulation reaction, according to the following Scheme 2:

Scheme 2

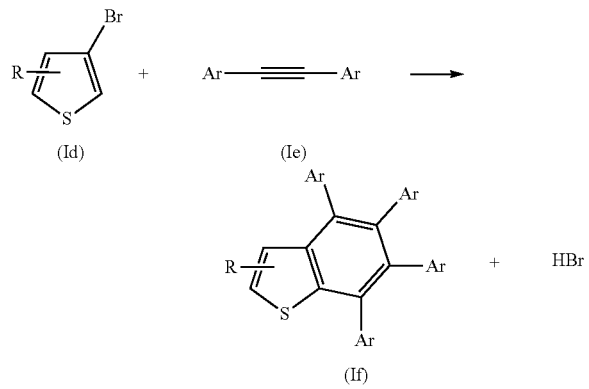

wherein a bromothiophene having formula (Id) such as, for example, 3-bromothiophene, is reacted with an internal alkyne having formula (Ie) such as, for example, diphenylacetylene, in the presence of a catalyst containing palladium such as, for example, palladium(II)acetate ([Pd(OAc)$_2$]), a phosphine such as, for example, tricyclohexylphosphine (PCy$_3$), a solvent such as, for example, dimethylformamide (DMF), and a base such as, for example, sodium carbonate (Na$_2$CO$_3$), obtaining a tetra-aryl-benzoalkyl-thiophene having formula (If).

Gericke K. M. et al., in the article: "The versatile role of norbornene in C—H functionalization processes: concise synthesis of tertracyclic fused pyrroles via a threefold domino reaction", "*Tetrahedron*" (2008), Vol. 64, pg. 6002-6014, describe an annulation reaction according to the following Scheme 3:

Scheme 3

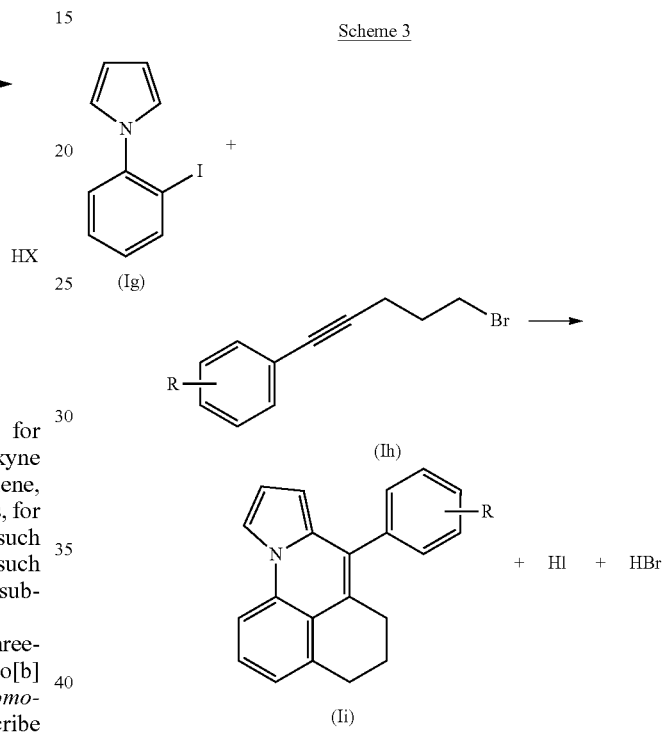

wherein an aryl iodide such as, for example, 1,2-iodophenyl-1-H-pyrrole having formula (Ig), is reacted with an internal bromo-alkylarylalkyne having formula (Ih) such as, for example, (5-bromo-1-pentenyl)benzene, in the presence of a catalyst containing palladium such as, for example, palladium(II)chloride (PdCl$_2$) associated with triphenylphosphine (PPh$_3$) as ligand, in the presence of a solvent such as, for example, acetonitrile (CH$_3$CN), and a base such as, for example, caesium carbonate (Cs$_2$CO$_3$), obtaining a 7-phenyl-5,6-dihydro-4H-benzo[de]pyrrole[1,2-α]-quinoline having formula (Ii).

Italian patent application MI 2011 A002303 in the name of the Applicant, describes a process for the preparation of benzodithiophene compounds which comprises reacting at least one monohalogenated dithiophene compound with at least one internal alkyne, in the presence of a dipolar aprotic organic solvent, a weak organic base and a catalyst containing palladium (Pd), at a temperature ranging from 80 to 170° C., for a time ranging from 30 to 72 hours.

Even if the above process for the preparation of benzodithiophene compounds allows the desired products to be obtained with good yields (80%), it requires a high number of synthesis passages and consequently longer processing times and higher process costs. There is also the production of halogenated salts and therefore higher disposal costs.

The Applicant has therefore considered the problem of finding a process for the preparation of a benzodithiophene compound capable of overcoming the drawbacks indicated above. In particular, the Applicant has considered the problem of finding a process for the preparation of a benzodithiophene compound by means of an annulation reaction starting from a dithiophene compound.

Processes for the preparation of polycyclic aromatic compounds through annulation reactions of non-halogenated diaryl compounds with internal alkynes, (annulation reactions via direct dehydrogenation DDA) in the presence of palladium compounds as catalysts, are known in the art.

Jiao N. et al., for example, in the article: "A Palladium-Catalyzed Oxidative Cycloaromatization of Biaryls with Alkynes Using Molecular Oxygen as the Oxidant", "*Angewandte Chemie International Edition*" (2009), Vol. 48, pages 7895-7898, describe an annulation reaction via direct dehydrogenation with internal alkynes according to the following Scheme 4:

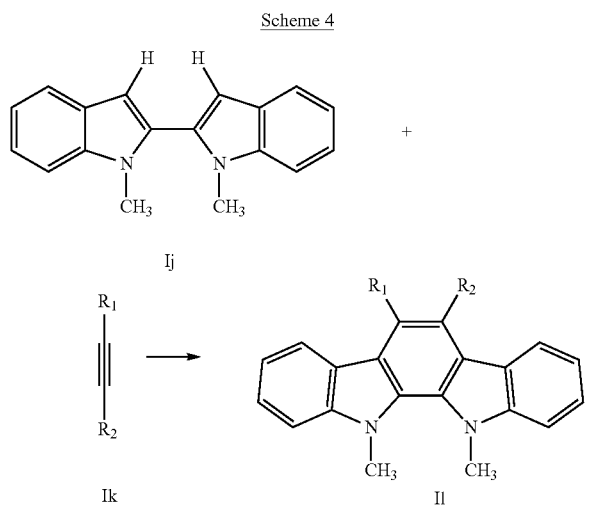

wherein a diaryl compound having formula (Ij) such as, for example, 2,2'-bis(N-methylindolyl), is reacted with an internal alkyne having formula (Ik) such as, for example, diphenylacetylene, in the presence of a catalyst containing palladium such as, for example, palladium(II)acetate ([Pd(OAc)$_2$]), a solvent such as, for example, dimethylformamide (DMF), and a base such as, for example, potassium carbonate ($K_2CO_3$) and a quaternary ammonium salt such as, for example, tetrabutylammonium bromide (TBAB), obtaining a disubstituted polycyclic aromatic compound having formula (Il).

Miura M. et al., in the article "Rhodium-Catalyzed Oxidative Coupling/Cyclization of 2-Phenylindoles with Alkynes via C—H and N—H Bond Cleavages with Air as the Oxidant", "*Organic Letters*" (2010), Vol. 12, pages 2068-2071, describe an annulation reaction via direct dehydrogenation with internal alkynes catalyzed by complexes of rhodium, according to the following Scheme 5:

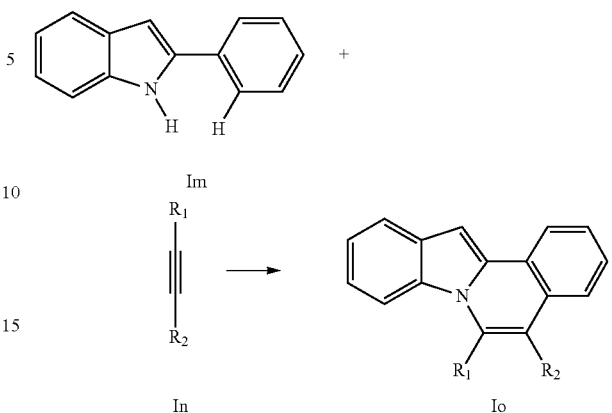

wherein an indole having formula (Im) such as, for example, phenylindole, is reacted with an internal alkyne having formula (In) such as, for example, diphenylacetylene, in the presence of a catalyst containing rhodium such as, for example, pentamethylcyclopentadienyl rhodium(III) chloride dimer [Cp*RhCl$_2$]$_2$, a copper salt such as copper(II) acetate ([Cu(OAc)$_2$]), a base such as, for example, sodium carbonate $Na_2CO_3$, a solvent such as, for example, o-xylene, obtaining a polycyclic aromatic compound having formula (Io).

The Applicant has now found that the preparation of benzodithiophene compounds can be advantageously effected by means of a process which comprises reacting 3,3'-bithiophene with at least one internal alkyne. The benzodithiophene compounds obtained with the process of the present invention can be suitably functionalized and polymerized to give electron-donor compounds which can be used in photovoltaic devices. Furthermore, said benzodithiophene compounds can be advantageously used as spectrum converters in luminescent solar concentrators and as precursors of monomeric units in the preparation of semiconductor polymers.

There are numerous advantages obtained by operating according to the above process such as, for example:

reduction in the number of synthesis steps with a relative reduction in the processing times and process costs;

use of non-halogenated starting products generally more economical and more stable than the corresponding mono- and dihalogenated compounds, therefore the production of lower quantities of waste-products with a consequent reduction in the disposal costs;

use of more economical and more stable internal alkynes with respect to diboron esters of internal alkenes;

greater safety conditions [e.g. absence of toxic and explosive reagents such as, for example, titanium tetrachloride, butyl lithium, lithium diisopropylamide (LDA)] for both the health of the operators and from an environmental point of view;

relatively short reaction temperatures and times thus avoiding the possible degradation of the product obtained and higher process costs.

An object of the present invention therefore relates to a process for the preparation of a benzodithiophene compound having general formula (I):

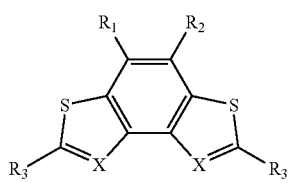

wherein:
R$_1$ and R$_2$ are each independently selected from a hydrogen atom, a linear or branched C$_1$-C$_{20}$, preferably C$_1$-C$_{12}$, alkyl group, a cycloalkyl group and an aryl group, said groups being optionally substituted;
R$_3$ is selected from:
a hydrogen atom H, —CHO or —CN;
a group selected from R, —OR, —COR, —COOR and R—O—[CH$_2$—CH$_2$—O]$_n$— wherein R is a linear or branched C$_1$-C$_{20}$, preferably C$_1$-C$_{12}$, alkyl group, a cycloalkyl group optionally substituted or an aryl group optionally substituted, and n is an integer ranging from 1 to 4;
a —R'OR$_4$ group wherein R' represents a linear or branched C$_1$-C$_{20}$, preferably C$_1$-C$_{12}$, alkylene group and R$_4$ is selected from H, a linear or branched C$_1$-C$_{20}$, preferably C$_1$-C$_{12}$, alkyl group, and a polyethyleneoxyl group R$_5$—[—OCH$_2$—CH$_2$—]$_n$— wherein R$_5$ is a C$_1$-C$_{20}$, preferably C$_1$-C$_{12}$, alkyl group and n is an integer ranging from 1 to 4;
X is selected from a nitrogen atom and a CR$_6$ group, wherein R$_6$ is selected from a hydrogen atom, a linear or branched C$_1$-C$_{20}$, preferably C$_1$-C$_{12}$, alkyl group, a cycloalkyl group optionally substituted, an aryl group optionally substituted, a heteroaryl group optionally substituted, a —CHO group, a —CN group, a Y group selected from —COR, a —COOR group, and a —CONR$_2$ group, wherein R is selected from a linear or branched C$_1$-C$_{20}$, preferably C$_1$-C$_{12}$, alkyl group, a cycloalkyl group optionally substituted and an aryl group optionally substituted,
wherein said process comprises reacting a derivative of 3,3'-bithiophene having formula (II):

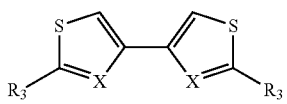

wherein X and R$_3$ have the same meanings described above, with at least one internal alkyne having general formula (III)

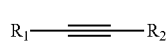

wherein R$_1$ and R$_2$ have the meanings described above.

For the purposes of the present description and following claims, the definitions of the numerical intervals always include the extremes, unless otherwise specified.

The term "C$_1$-C$_{20}$ alkyl group" means a linear or branched alkyl group having from 1 to 20 carbon atoms. Said alkyl group can be optionally substituted with one or more groups, equal to or different from each other, selected from: halogen atoms such as, for example, fluorine, chlorine, preferably fluorine, hydroxyl groups, C$_1$-C$_{20}$ alkyl groups, C$_1$-C$_{20}$ alkoxyl groups, cyano groups, amino groups, nitro groups. Specific examples of a C$_1$-C$_{20}$ alkyl group are: methyl, ethyl, n-propyl, iso-propyl, n-butyl, iso-butyl, t-butyl, pentyl, ethylhexyl, hexyl, heptyl, octyl, nonyl, decyl, dodecyl.

The term "cycloalkyl group" means a cycloalkyl group having from 3 to 10 carbon atoms. Said cycloalkyl group can be optionally substituted by one or more groups, equal to or different from each other, selected from: halogen atoms, such as, for example, fluorine, chlorine, preferably fluorine; hydroxyl groups; C$_1$-C$_{20}$ alkyl groups; C$_1$-C$_{20}$ alkoxyl groups; cyano groups; amino groups; nitro groups. Specific examples of a cycloalkyl group are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl group" means an aromatic carbocyclic group. Said aromatic carbocyclic group can be optionally substituted with one or more groups, equal to or different from each other, selected from: halogen atoms such as, for example, fluorine, chlorine, preferably fluorine; hydroxyl groups; C$_1$-C$_{20}$ alkyl groups; C$_1$-C$_{20}$ alkoxyl groups, cyano groups; amino groups; nitro groups. Specific examples of an aryl group are: phenyl, methylphenyl, trimethylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene.

The above process therefore corresponds to the following reaction scheme:

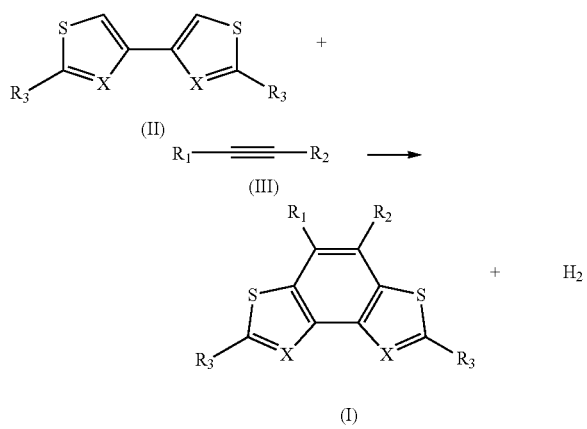

A preferred aspect of the present invention is preparing compounds having formula (IA):

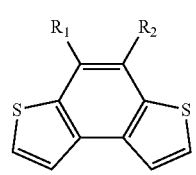

wherein R$_1$ and R$_2$ have the meanings indicated above, by reaction with 3,3'-bithiophene having formula (IIA)

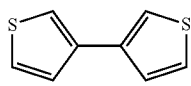

with an alkyne having general formula (III)

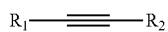

wherein $R_1$ and $R_2$ have the meanings indicated above.

According to said preferred aspect, the process of the present invention corresponds in particular to the following scheme:

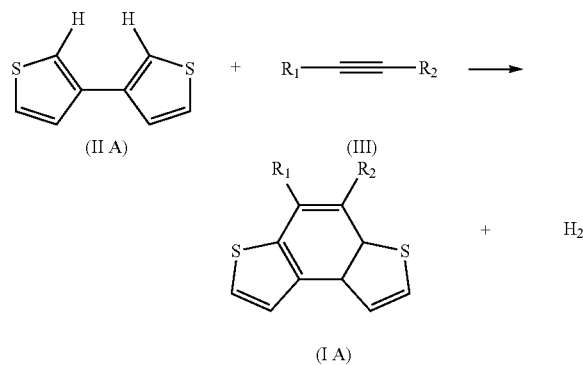

wherein $R_1$ and $R_2$ have the meanings indicated above.

According to a preferred embodiment of the present invention, the bithiophene compound having general formula (II) and the internal alkyne having formula (III) can be used in molar ratios ranging from 1:2 to 1:10, preferably ranging from 1:2 to 1:5.

According to a preferred embodiment of the present invention, benzodithiophene compounds having general formula (IA) are prepared, wherein $R_1$ and $R_2$ are $C_1$-$C_{20}$ alkyl groups, preferably the same, by reaction of 3,3'-bithiophene having formula (IIA), with an alkyne having general formula (III), wherein $R_1$ and $R_2$ represent a $C_1$-$C_{20}$, preferably $C_1$-$C_{12}$, alkyl group.

A particularly preferred aspect of the present invention is to prepare benzodithiophene compounds having general formula (IA), wherein $R_1$ and $R_2$ represent a $C_3$-$C_8$ alkyl group, by reaction of 3,3'-bithiophene having formula (IIA), with an alkyne having formula (III), wherein $R_1$ and $R_2$ represent $C_3$-$C_8$ alkyl groups, equal to or different from each other.

According to a further preferred embodiment of the present invention, said process relates to the preparation of 4,5-dibutylbenzo[1,2-b:4,3-b'] dithiophene corresponding to a benzodithiophene compound having formula (IA) wherein $R_1$ and $R_2$ represent an n-butyl group, said process comprising reacting 3,3'-bithiophene having formula (IIA), with 5-decyne corresponding to an internal alkyne having general formula (III), wherein $R_1$ and $R_2$ represent n-butyl groups.

According to a preferred embodiment of the present invention, said process is carried out in the presence of molecular oxygen.

According to a preferred embodiment of the present invention, said process is carried out in the presence of a weak organic base and a weak organic acid, using at least one catalyst based on Pd and at least one catalyst based on copper.

A weak organic base refers to an organic base preferably having a $pK_b$ lower than or equal to 4.67.

According to a preferred embodiment of the present invention, said weak organic base can be selected, for example, from: carboxylates of alkaline metals (e.g. sodium, potassium, caesium) or alkaline-earth metals (e.g. magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkaline metals (e.g. lithium, sodium, potassium, caesium) or alkaline-earth metals (e.g. magnesium, calcium) such as, for example, lithium carbonate, potassium carbonate, sodium carbonate, caesium carbonate, magnesium carbonate, calcium carbonate, or mixtures thereof; bicarbonates of alkaline metals (e.g. lithium, sodium, potassium, caesium) or alkaline-earth metals (e.g. magnesium, calcium) such as lithium bicarbonate, potassium bicarbonate, sodium bicarbonate, caesium bicarbonate, magnesium bicarbonate, calcium bicarbonate, or mixtures thereof; or mixtures thereof. Said weak organic base is preferably selected from potassium acetate and potassium carbonate.

According to a preferred embodiment of the present invention, said dithiophene compound having formula (II) and the weak organic base can be used in molar ratios ranging from 1:1 to 1:10, preferably ranging from 1:1.5 to 1:3.

Weak organic acid refers to an organic acid having a $pK_a$ preferably greater than or equal to 5.03.

According to a preferred embodiment of the present invention, said weak organic acid can be selected, for example, from carboxylic acids, for example, acetic acid, propionic acid, butanoic acid, pivalic acid. Said weak organic acid is preferably selected from acetic acid and pivalic acid.

According to a preferred embodiment of the present invention, said dithiophene compound having formula (II) and said weak organic acid can be used in molar ratios ranging from 1:0.1 to 1:1, preferably ranging from 1:0.2 to 1:0.5.

The process of the present invention is carried out in the presence of at least one catalyst containing palladium.

According to a preferred embodiment of the present invention, said catalyst containing palladium can be selected from: compounds of palladium in oxidation state (0) or (II): for example can be used palladium(II)chloride [$PdCl_2$], palladium(II)acetate [$Pd(OAc)_2$], bis(dibenzylidene)palladium(0) [$Pd_2(dba)_3$ wherein dba $=C_6H_5CH=CHCOCH=CHC_6H_5$], bis(acetonitrile)-palladium (II) chloride [$Pd(CH_3CN)_2Cl_2$], bis(tri-phenylphosphine)palladium(II) chloride [$Pd(PPh_3)_2Cl_2$], bis(triphenylphosphine)-palladium(II) acetate [$Pd(PPh_3)_2(OAc)_2$], tetrakis-(triphenylphosphine)-palladium(0) [$Pd(PPh_3)_4$], or mixtures thereof. Said catalyst containing palladium is preferably selected from palladium (II) acetate [$Pd(OAc)_2$] and bis(tri-phenylphosphine)palladium(II) chloride [$Pd(PPh_3)_2Cl_2$].

According to a preferred embodiment of the present invention, said dithiophene compound having formula (II) and the palladium contained in the catalyst can be used in molar ratios ranging from 100:1 to 100:15, preferably ranging from 100:5 to 100:10.

According to a preferred embodiment of the present invention, said dithiophene compound having formula (II) can be used at a concentration ranging from 0.05 Molar (M) to 2 Molar (M), preferably ranging from 0.1 Molar (M) to 1.5 Molar (M), with respect to the solvent.

The catalyst containing copper preferably contains it in oxidation state (II), for example copper(II) acetate [Cu(OAc)$_2$] can be used.

According to a preferred embodiment of the present invention, said dithiophene compound having general formula (II) and said copper catalyst can be used in molar ratios between compound (II) and copper ranging from 1:0.2 to 1:1, preferably ranging from 1:0.3 to 1:0.6.

According to a preferred embodiment of the present invention, said process can be carried out in the presence of at least one dipolar aprotic organic solvent.

According to a preferred embodiment of the present invention, said dipolar aprotic organic solvent can be selected, for example, from N,N-dimethylacetamide (DMAc), dimethylsulfoxide (DMSO), N-methylpyrrolidone (NMP), N,N-dimethylformamide (DMF), and mixtures thereof. Said dipolar aprotic organic solvent is preferably selected from N,N-dimethylacetamide (DMAc) and N,N-dimethylformamide (DMF).

According to a preferred embodiment of the present invention, said process can be carried out in the presence of at least one quaternary ammonium salt such as, for example, a tetraalkylammonium bromide, preferably tetra-butylammonium bromide.

According to a preferred embodiment of the present invention, said bithiophene compound having formula (II) and said quaternary ammonium salt can be used in molar ratios ranging from 1:0.5 to 1:5, preferably ranging from 1:0.8 to 1:2.

According to a preferred embodiment of the present invention, said process can be carried out at a temperature ranging from 80° C. to 170° C., preferably ranging from 100° C. to 150° C.

According to a preferred embodiment of the present invention, said process can be carried out for a time ranging from 30 minutes to 72 hours, preferably ranging from 3 hours to 48 hours.

The dithiophene compound having formula (II) can be obtained according to processes known in the art, for example, by coupling reaction catalyzed by palladium compounds. Further details relating to said processes can be found, for example, in the article of Bredow T. et al.: "Syntheses and properties of thienyl-substituted dithienophenazines" *Beilstein Journal of Organic Chemistry*" (2010), Vol. 6, pages 1180-1187; or in the article of Zhang Y. et al.: "Palladium-Catalyzed Homocoupling and Cross-Coupling Reactions of Aryl Halides in Poly(ethylene glycol)", "*Journal of Organic Chemistry*" (2006), Vol. 71, pages 1284-1287.

The internal alkyne having general formula (III) is easily available on the market, or it can be prepared according to processes known in the art, for example, by nucleophilic substitution of an alkyl acetylide on an alkyl halide as described, for example, in the article of Kirkham J. E. D. et al.: "Asymmetric synthesis of cytotoxic sponge metabolites R-strongylodiols A and B", "*Tetrahedron Letters*" (2004), Vol. 45, No. 29, pages 5645-5648.

An illustrative and non-limiting example is provided for a better understanding of the present invention and for its practical embodiment.

EXAMPLE 1

Preparation of 4,5-dibutylbenzo[1,2-b:4,3-b']dithiophene having formula (b)

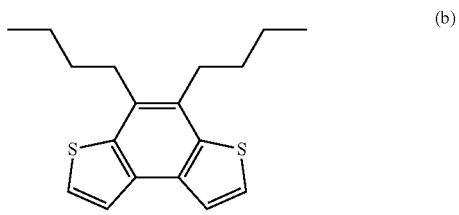

The following products were charged in order into a 100 mL two-necked pyrex glass flask equipped with a cooler: 249 mg of potassium carbonate (1.8 mmoles), 613 mg of pivalic acid (6 mmoles), 967 mg of tetrabutylammonium bromide (3 mmoles), 135 mg of palladium(II)acetate [Pd(OAc)$_2$] (0.6 mmoles), 599 mg of copper(II)acetate [Cu(OAc)$_2$] (3 mmoles), 996 mg of 3,3'-dithiophene (6 mmoles) dissolved in 40 ml of N,N-dimethylacetamide and finally 2.488 g of 5-decine (18 mmoles). The reaction mixture was put in an oxygen atmosphere and heated to 100° C. for 16 hours. After cooling to room temperature (25° C.), a saturated aqueous solution of sodium chloride (250 ml) was added to the reaction mixture and the whole mixture was extracted with ethyl acetate (3×200 ml). The organic phase obtained was washed to neutrality with water (3×250 ml) and subsequently anhydrified on sodium sulfate and evaporated. The residue obtained was purified by elution on a chromatographic column of silica gel (eluent: heptane), obtaining 546 mg of 4,5-dibutylbenzo[1,2-b:4,3-b']dithiophene as a white solid (yield 30%).

The invention claimed is:

1. A process for the preparation of a benzodithiophene compound having general formula (I):

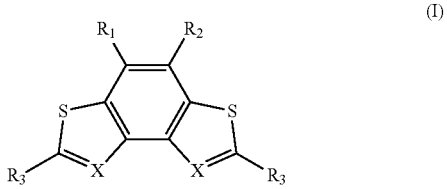

wherein:
R$_1$ and R$_2$ are each independently selected from a hydrogen atom, a linear or branched C$_1$-C$_{20}$ alkyl group, a cycloalkyl group and an aryl group, said groups being optionally substituted;
R$_3$ is selected from:
a hydrogen atom H, —CHO or —CN;
a group selected from R, —OR, —COR, —COOR and R—O—[CH$_2$—CH$_2$—O]$_n$— wherein R is a linear or branched C$_1$-C$_{20}$ alkyl group, a cycloalkyl group optionally substituted or an aryl group optionally substituted, and n is an integer ranging from 1 to 4;

a —R'OR$_4$ group wherein R' represents a linear or branched C$_1$-C$_{20}$ alkylene group and R$_4$ is selected from H, a linear or branched C$_1$-C$_{20}$ alkyl group, and a polyethyleneoxyl group R$_5$—[—OCH$_2$—CH$_2$—]$_n$— wherein R$_5$ is a C$_1$-C$_{20}$ alkyl group and n is an integer ranging from 1 to 4;

X is selected from a nitrogen atom and a CR$_6$ group, wherein R$_6$ is selected from a hydrogen atom, a linear or branched C$_1$-C$_{20}$ alkyl group, a cycloalkyl group optionally substituted, an aryl group optionally substituted, a heteroaryl group optionally substituted, a —CHO group, a —CN group, a Y group selected from —COR, a —COOR group, and a —CONR$_2$ group, wherein R is selected from a linear or branched C$_1$-C$_{20}$ alkyl group, a cycloalkyl group optionally substituted and an aryl group optionally substituted, wherein said process comprises reacting a derivative of 3,3'-bithiophene having general formula (II):

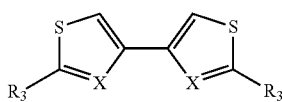

(II)

wherein X and R$_3$ have the same meanings described above, with at least one internal alkyne having general formula (III)

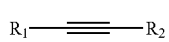

(III)

wherein R$_1$ and R$_2$ have the meanings described above.

2. The process according to claim 1 for preparing compounds having formula (IA):

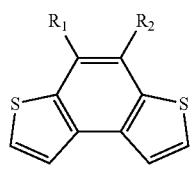

(IA)

wherein said process comprises reacting 3,3'-bithiophene having formula (IIA)

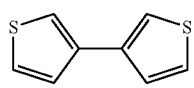

(IIA)

with an alkyne having general formula (III)

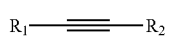

(III)

wherein R$_1$ and R$_2$ are each independently selected from a hydrogen atom, a linear or branched C$_1$-C$_{20}$ alkyl group, a cycloalkyl group and an aryl group, said groups being optionally substituted.

3. The process according to claim 1, wherein the molar ratio between the derivative of 3,3'-bithiophene having formula (II) and the alkyne having formula (III) ranges from 1:2 to 1:10.

4. The process according to claim 1, wherein R$_1$, R$_2$, R, R', R$_4$, R$_5$, R$_6$ groups, are each independently a C$_1$-C$_{12}$ alkyl group.

5. The process according to claim 2, wherein R$_1$ and R$_2$ are C$_1$-C$_{20}$ alkyl groups, the same or different.

6. The process according to claim 5, wherein R$_1$ and R$_2$ are C$_1$-C$_{12}$ alkyl groups, the same or different.

7. The process according to claim 6, wherein R$_1$ and R$_2$ are C$_3$-C$_8$ alkyl groups, the same or different.

8. The process according to claim 7, wherein R$_1$ and R$_2$ are n-butyl groups.

9. The process according to claim 1, carried out in the presence of molecular oxygen.

10. The process according to claim 1, carried out in the presence of a weak organic base and a weak organic acid, using at least one catalyst based on palladium and at least one catalyst based on copper.

11. The process according to claim 10, wherein the weak organic base is an organic base having a pK$_b$ lower than or equal to 4.67.

12. The process according to claim 10, wherein the molar ratio between the bithiophene compound having formula (II) and the weak organic base ranges from 1:1 to 1:10.

13. The process according to claim 10, wherein the weak organic acid is an organic acid having a pK$_a$ higher than or equal to 5.03.

14. The process according to claim 10, wherein the molar ratio between the bithiophene compound having formula (II) and the weak organic acid ranges from 1:0.1 to 1:1.

15. The process according to claim 10, wherein said catalyst containing palladium is selected from palladium compounds in oxidation state (0) or (II).

16. The process according to claim 10, wherein said catalyst containing copper, contains it in oxidation state (II).

17. The process according to claim 10, wherein the molar ratio between the bithiophene compound having formula (II) and the palladium contained in the catalyst ranges from 100:1 to 100:15.

18. The process according to claim 10, wherein the molar ratio between the bithiophene compound having formula (II) and copper ranges from 1:0.2 to 1:1.

19. The process according to claim 1, carried out in the presence of a solvent, wherein the bithiophene compound having formula (II) is used at a concentration ranging from 0.05 molar to 2 molar with respect to the solvent.

20. The process according to claim 1, carried out in the presence of a solvent, wherein said solvent is an aprotic, dipolar organic solvent or a mixture of said solvents.

21. The process according to claim 1, carried out in the presence of at least one ammonium quaternary salt.

22. The process according to claim 21, wherein the bithiophene compound having formula (II) and the quaternary ammonium salt are used in a molar ratio ranging from 1:05 to 1:5.

23. The process according to claim 1, carried out at a temperature ranging from 80° C. to 170° C.

* * * * *